United States Patent [19]

Dodak et al.

[11] 4,309,992
[45] Jan. 12, 1982

[54] MICROBICIDAL FILTER

[76] Inventors: Michael J. Dodak, 116 Avenida Dolores, San Clemente, Calif. 92672; Charles R. Whitlock, 10454 Gloria Ave., Granada Hills, Calif. 91344

[21] Appl. No.: 167,507

[22] Filed: Jul. 11, 1980

[51] Int. Cl.³ .............................................. B01D 27/00
[52] U.S. Cl. ................. 128/213 A; 210/266; 210/282; 210/927
[58] Field of Search ....................... 128/213 A, 214 R; 210/668, 764, 427, 266, 282, 286, 287, 289, 291, 314, 316–318, 501; 252/447

[56] References Cited

U.S. PATENT DOCUMENTS 1,432,351 10/1922 McGahan ............................ 210/286
3,901,808 8/1975 Bokros ................................. 210/927
4,045,553 8/1977 Mitsumori et al. ................. 210/501
4,048,064 9/1977 Clark ................................... 210/282

FOREIGN PATENT DOCUMENTS 740539 4/1970 Belgium ......................... 128/213 A

*Primary Examiner*—Ivars C. Cintins
*Attorney, Agent, or Firm*—Nilsson, Robbins, Dalgarn, Berliner, Carson & Wurst

[57] ABSTRACT

A method and apparatus for removing living microorganisms from fluid to be introduced in vivo, wherein the fluid is passed through a filter comprising a tubular passage having a plurality of filter elements coated with a microbicidal material, e.g., silver. In one embodiment, the filter element is hermetically sealed until attached by the patient to the external end of a cannula or other body-penetrating apparatus. In addition, an embodiment is disclosed wherein the filter is integral with the external portion of the cannula or other body-penetrating apparatus and has a removable top for removing and replacing spent filter elements, which may be done under sterile hospital conditions and the top re-sealed in place. A further embodiment is in the form of an auxiliary filter element which may be placed on the external end of the body-penetrating apparatus in a medically sterile environment, e.g., a hospital or doctor's office, and adapted to be attached to the discharge of a filter element when self-applied by a patient, in order to remove any microorganisms collected in the self-applied filter, downstream of the microbicidal filter elements, between uses of the self-applied filter by the patient.

2 Claims, 5 Drawing Figures

MICROBICIDAL FILTER

BACKGROUND AND SUMMARY OF THE INVENTION

In the field of medicine in which it is often necessary to inject a fluid, i.e., a solution containing certain nutrients or medications, or for the purpose of impurity exchange and removal, as in peritoneal dialysis, a severe problem exists due to infection caused by the injection of infection-causing microorganisms along with the solution. Examples of the injection of such solutions include intravenous injection of nutrients and/or medications and, as noted above, peritoneal dialysis. During intravenous injection, a solution bag containing the desired solution is connected through tubing and an intravenous needle directly into the vein of a patient. Peritoneal dialysis, which has the great advantage of using a small light-weight system which the patient can attach and detach on his own, outside of a hospital or doctor's office, involves the permanent installation in the patient of a body-penetrating apparatus, e.g., a cannula. The cannula penetrates the body and pierces the peritoneum with the body-penetrating end thereof opening into the peritoneal cavity. The external end of the cannula has an opening to which the patient can attach tubing connected to a suitable reservoir, e.g., an IV bag, for a dialysis solution. During the dialysis, the solution from the IV bag is gravity-drained through the tubing and the cannula into the peritoneal cavity. The tubing is then detached from the cannula and the solution allowed to remain in the peritoneal cavity for a period of time during which impurities from the bloodstream are removed through osmosis through the peritoneum. The patient then reattaches tubing to the cannula and the dialysis solution is drained by gravity from the peritoneal cavity, removing along wih the dialysis solution the impurities transferred to the solution through the peritoneum.

While IV's are normally administered to the patient in the sterile environment of, e.g., a hospital, at times the IV must be placed on the patient in the field, as, e.g., at the scene of an accident. In such cases, the danger exists of possibly introducing microorganisms into the IV bag or the tubing connecting the IV bag to the intravenous needle. In addition, even when the IV is administered to the patient in the sterile environment of the hospital or doctor's office, manufacturing errors during the fabrication of the IV bag, its solution contents, or the connecting tubing, also create some danger that microorganisms, which can cause infection, might be contained within the IV bag, its solution contents, or the tubing, or the connection between the tubing and the intravenous needle.

The problem of potential injection of infection-causing microorganisms is even more severe in the peritoneal dialysis situation. This potential infection-causing problem is presently the major drawback to the otherwise extremely beneficial advantages of peritoneal dialysis. Ailments which necessitate treatment through dialysis strike patients in all socio-economic levels and patients having widely varying degrees of intelligence and/or habits of cleanliness or the practice of taking sterile precautions when connecting the tubing for the dialysis solution to the external end of the cannula. The danger thus exists that patients, to varying degrees, will be susceptible to the injection of infection-causing microorganisms when making the necessary connections for self-administered peritoneal dialysis.

Filters for separating substances contained in a suspension in a fluid, e.g., a solution, have been well known in the medical arts. Mechanical filters constructed of a material such as cloth which will absorb certain materials, but not others, or filters using mechanical means, e.g., metal grating or metal particles and accomplishing filtration by limiting the size of the allowable particles which can pass through the mechanical restrictions, are also well known in the art. Filtration by ion exchange is also well known, in which a bed of filter elements which have certain ions loosely bound thereto and a stronger affinity for other ions desired to be removed from the solution, than the affinity for the loosely-bound ions, will exchange ions with the solution, thus removing the undesirable ions. In addition, various other filtrations, e.g., filtrations through chemical means, are known in the art.

In the past, microorganisms, e.g., bacteria, have been filtered in medical devices by mechanical means, e.g., by screening, or by chemical means, in which anti-bacterial agents, e.g., iodine, are placed in the path of the fluid from which the microorganisms are desired to be removed, e.g., by impregnating a cloth filter with antibacterial agents. The use of antiseptic techniques during patient treatment, including surgical gloves and clean and careful handling methods, are also techniques of preventing microorganisms from entering the body of the patient, i.e., "filtering" the microorganisms from entering an opening in the body.

It is also known in the art to use activated carbon which has been impregnated on its surface with silver during various sterilization and purification procedures well known in the medical arts. These methods of impregnating silver on the surface of activated carbon are shown, e.g., in U.S. Pat. No. 3,294,572. However, in the course of such usage, organic substances accumulate on the surface of the silver-impregnated material resulting in a large reduction in the silver impregnated material's capacity to effectively sterilize. In addition, the silver-impregnated carbon systems kill the microorganism, e.g., bacteria, via a sustained release of silver ions into the filtered solution. High concentrations of silver ion are needed to relatively rapidly kill the microorganisms, e.g., bacteria. This requires scavenger systems to be utilized to remove or sufficiently lower the silver ion concentration to physiologically safe levels prior to the introduction of any such filtered and sterilized solution into the body of a patient.

Mechanical filtering elements which have a sufficiently small porosity to filter microorganisms, e.g., micropore filters, would create such a substantial delay in the transfer of the IV or dialysis solution through the filter as to result in an exceedingly large time, on the order of days, for sufficient solution to be injected into the body of the patient to have the beneficial results desired.

The present invention, therefore, relates to a method and apparatus for removing living microorganisms from a fluid to be introduced in vivo, wherein the fluid is passed through a filter comprising a tubular passage having a plurality of filter elements coated with a microbicidal material, e.g., silver.

The problems enumerated in the foregoing discussion are not intended to be exhaustive, but rather are among many which tend to impair the effectiveness of methods and apparatus for injecting fluid in vivo, particularly when self-administered by the patient, and the use of known filter elements capable of removing microorganisms from such solution prior to injection. Other noteworthy problems may also exist; however, those presented above should be sufficient to demonstrate that the prior art has not been altogether satisfactory.

Examples of the more important features of the present invention have been summarized rather broadly in order that the detailed description thereof that follows may be better understood and in order that the contribution to the art may be better appreciated. There are, of course, additional features of the invention that will be described hereinafter and which will also form the subject of the appended claims. These other features and advantages of the present invention will become more apparent with reference to the following detailed description of a preferred embodiment thereof in connection with the accompanying drawings, wherein like reference numerals have been applied to like elements, in which:

DETAILED DESCRIPTION OF THE PREFERRED EMBODIMENTS

Figure 1:
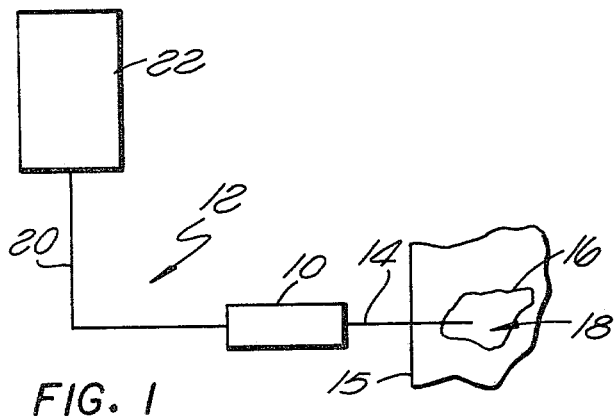
FIG. 1 shows a schematic view of an in vivo injection method and apparatus, e.g., for peritoneal dialysis, incorporating the method and apparatus for filtering infection-causing microorganisms according to the present invention.

Turning now to FIG. 1, there is shown schematically a microbicidal filter 10 according to the present invention contained in a system used for injecting a fluid, e.g., a solution containing nutrients and/or medications or for the purpose of peritoneal dialysis into the body of a patient. The system 12 is shown to be for peritoneal dialysis and includes a cannula 14 which penetrates the skin 15 of the patient and pierces the peritoneum 16 opening into the peritoneal cavity 18. The external end of the cannula 14 is attached to the filter 10 according to the present invention. Tubing 20 connects the filter 10 with a suitable reservoir 22 for containing the dialysis solution which may be, e.g., a plastic IV bag.

Figure 2:
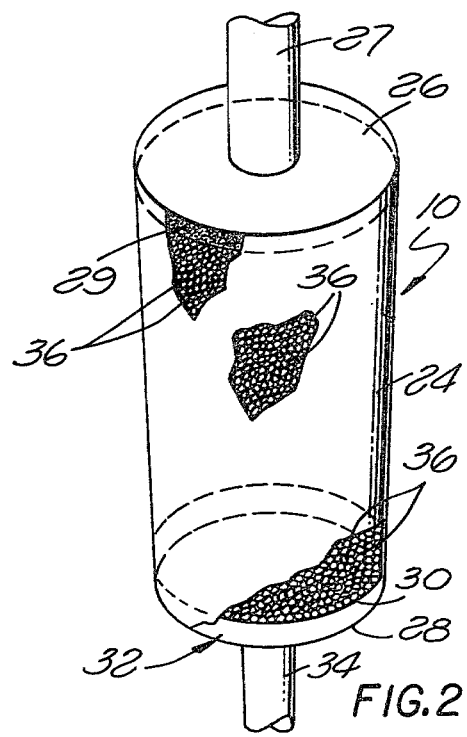
FIG. 2 shows a microbicidal filter according to the present invention which contains a plurality of filter elements packed within the filter, each composed of or coated with a microbicidal material.

FIG. 2 shows the filter 10, illustrated schematically in FIG. 1, in greater detail. The filter 10 has a hollow tubular casing 24 which is closed on both ends thereof by a first enclosure plate 26 and a second enclosure plate 28. The casing 24 and the enclosure plates 26, 28 may be of any suitable material having sufficient strength and rigidity, e.g., polyvinyl chloride plastic. An inlet coupling tube 27 is formed integrally with the first enclosure plate 26 with the tube 27 forming an opening in the first enclosure plate 26. Disposed within the casing 24 near the opening of the tube 27 through the first enclosure plate 26 is an inlet porous plate 29. Also contained within the casing 24 is an outlet porous plate 30 which is disposed away from the second closure plate 28 forming therebetween an outlet plenum 32. A tubular outlet coupling 34 is formed integrally with the second enclosure plate 28 and forms an opening through the enclosure plate 28 into the outlet plenum 32.

Contained within the casing 24 between the porous plates 29, 30 are a plurality of tightly packed filter elements 36. The filter elements are fabricated from or coated with a material having microbicidal properties and may be for example pure silver spheres or silver-plated carbon spheres, since silver is highly toxic to microorganisms, fungi, slime, mold and bacteria. The microbicidal or bactericidal effects of silver are much greater in soft, pure water than in hard water or water containing appreciable concentrations of other metal ions. However, since physiological solutions are prepared with soft water, the effects of the silver will not be diminished for the reason of other metal ions being present in the solution. Other metals having microbicidal properties may be used, e.g., gold, copper, mercury and lead or alloys thereof. The inlet and outlet porous plates 29, 30 are sufficiently porous to not significantly impede the flow of solution through the filter 10, while still preventing any filter element 36 from passing through the inlet or outlet porous plates 29, 30.

Figure 3:
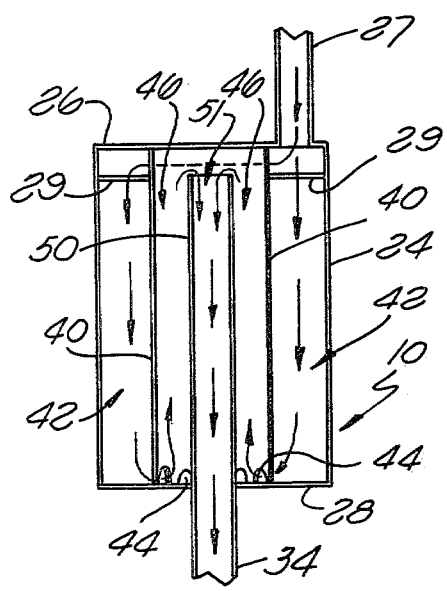
FIG. 3 shows a cross-sectional view of an alternative embodiment of the filter according to the present invention having inner and outer cavities containing the filter elements and in fluid communication so that the solution will pass through the outer chamber and the inner chamber prior to entering the discharge tube of the filter.

Turning now to FIG. 3, a cross-sectional view of an alternative embodiment of the microbicidal filter 10 according to the present invention is shown. Within the tubular casing 24, is a tubular inside wall 40 which extends from the first enclosure plate 26 to the second enclosure plate 28. An elongated donut-shaped outer passage 42 is defined between the casing 24 and the tubular inner wall 40. The tubular inlet coupling 27 is disposed off center on the first enclosure plate 26 and opens into the outer passage 42. The inlet porous plate 29 is also donut-shaped and is disposed between the casing 24 and the tubular inside wall 40 and defines an inlet plenum between the donut-shaped inlet porous plate 29 and the first enclosure plate 26. A plurality of holes 44 in the outlet end of the tubular inside wall which provide fluid communication between the outer passage 42 and an inner passage 46 within the enclosure of the tubular inner wall 40. An extension 50 of the tubular outlet coupling 34 is contained within the inner passage 46 and extends approximately the entire length of the inner passage 46 leaving an opening 51 at the end thereof and generally adjacent the first enclosure plate 26. As shown by the arrows in FIG. 3, the solution enters through the tubular inlet coupling 27 passes through the outer passage 42 and into the inner passage 46 through the openings 44, travelling in the reverse direction through the inner passage 46 and into the opening 51 in the extension 50 of the tubular outlet coupling 34 and thence out of the filter 10 through the tubular outlet coupling 34. The two passes thus double the length of travel of the solution through the filter elements (not shown in FIG. 3) for a given length of the tubular casing 24 of the filter 10.

In each of the embodiments shown in FIGS. 2 and 3, the filter 10 along with the tubular inlet coupling 27 and tubular outlet coupling 34 may be hermetically sealed by the manufacturer and remain hermetically sealed until the first use by the patient, and may also contain fittings for attaching the tubular inlet coupling 27 to the tube 20 shown in FIG. 1 and for attaching the tubular outlet coupling 34 to the body-penetrating apparatus, for example, the cannula 14 shown in FIG. 1. In either of the embodiments shown in FIGS. 2 and 3, the filter 10 may be attached to the body-penetrating apparatus, e.g., the cannula 14 shown in FIG. 1 in a suitable sterile and antiseptic environment, e.g., a doctor's office or hospital. In such a sterile and antiseptic environment, additional precautions, for example, the use of sterile surgical gloves and of topically-applied antiseptics, can be used to insure that the external portion of the, e.g., cannula 14, and the junction between the, e.g., cannula 14 and the tubular outlet coupling 34, are free of any living microorganisms when the junction between the cannula 14 and the tubular outlet coupling 34 is made.

The small size and light weight of the filter 10 can then enable the patient to continuously wear the filter 10 at all times between in vivo injections of fluid, e.g., dialysis fluid, during the safe life of the filter 10. The safe life of the filter 10 will depend upon the size of the filter 10 and the total surface area of the filter elements 36 contained within the filter 10. Since most of the living microorganisms will be destroyed by the coating on the filter elements in the first few fractions of an inch of the passage of the solution through the filter 10 during the early life of the filter, downstream filter elements will not begin to lose microbicidal effectiveness until the filter elements 36 in the initial portion of the solution-flow passage through the filter 10 has decreased to a point where microorganisms within the solution will reach the downstream filter elements. Thus the filter will have a generally predictable life during which it can be assured that essentially 100% of the living microorganisms will be removed from the solution passing through the filter 10. The filter 10 can be made of a sufficient size such that this useful life will last over a relatively large number of injections of the fluid, e.g., peritoneal dialysis fluid in vivo by the patient. It can thus be predicted for a given filter, within a certain factor of safety, when the patient should return to the doctor's office or hospital to have the filter removed and a new filter attached to the external end of the body-piercing apparatus, e.g., the cannula 14 under suitable sterile and antiseptic conditions. The size of the filter elements 36 may be varied as necessary for the desired flow rates of the fluid to be filtered and the viscosity of the fluid. For example, for a viscosity of between 0.8 and 1.10 and a flow rate of 10 to 300 cc/min the surface area of the filter elements 36 must total from 0.04 to 3.92 square inches with the requirement being 2.47 square inches for a preferred flow rate of 133 cc/min (2 liters/fifteen minutes). Based upon the total square inches of surface area initially and the rate of removal of the microbicidal material from the filter elements during filtering, the life of the filter 10 can be predicted, i.e., the amount of fluid which can be filtered before the available surface area drops below the needed surface area.

It may also be desirable for the patient to be able to remove the filter 10 between injections of fluid, e.g., peritoneal dialysis fluid, between dialysis treatment self-administered by the patient. The patient would thus not have to continuously wear the filter, and also the back-flushing of the peritoneal dialysis fluid through the filter 10 upon draining of the peritoneal cavity after the dialysis is completed, would not have an effect upon the useful life of the filter 10. In this instance, however, the danger would exist that the tubular outlet coupling 34, which would have to be made to be detachable from the external end of the cannula 14, with a suitable fitting for reattaching to the external end of the cannula 14, could, between dialysis treatments, be subject to becoming infected with microorganisms, e.g., bacteria. The external end of the, e.g., cannula 14, would also be subject to infectious microorganism invasion between treatments. Whatever microorganisms might infect the tubular outlet coupling 34 or external end of the cannula 14 would not be subjected to the microbicidal effect of the filter elements 36 when the filter 10 was reattached to the cannula 14 for a subsequent dialysis treatment.

Figure 4:
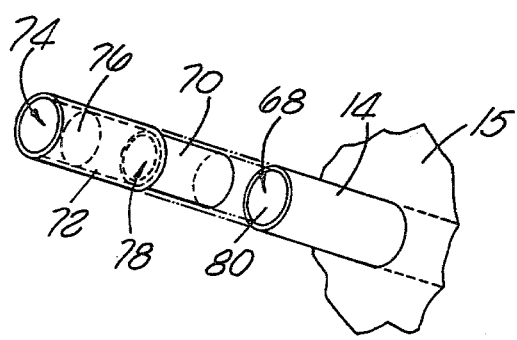
FIG. 4 shows an additional alternative embodiment of the filter according to the present invention which acts as an auxiliary filter connected to the external end of, e.g., a cannula.

An alternative embodiment of the invention, shown in FIG. 4, includes a tubular extension 72 of the cannula 14, which has a male fitting 70 for insertion into the opening 68 at the external end of the cannula 14. The tubular extension 72 has an inlet opening 74 into which a fitting (not shown) on the tubular outlet coupling 34 is inserted when it is desired to conduct the injection of fluid into the body of the patient, e.g., for a peritoneal dialysis treatment. The tubular extension 72 has an inlet porous plate 76 and an outlet porous plate 78 and contains a plurality of the above-described filter elements (not shown) packed between the inlet and outlet porous plates 76, 78. The tubular extension 72 can be attached to the external end of the cannula 14 under the sterile and antiseptic conditions, e.g., in a doctor's office or hospital, and be worn by the patient for its useful microbicidal life. The tubular extension 72 will act as an auxiliary filter for the filter 10 to remove any microorganisms which may infect the outlet tubular coupling 34 of the filter 10 or the inlet opening 74 of the auxiliary filter tubular extension 72 due to possible carelessness of the patient in handling the filter 10 or the external end 74 between dialysis treatments or during joining of the tubular outlet coupling 34 with the external end 74 of the cannula extension filter 72. The tubular extension auxiliary filte 72 may also serve as an emergency or reserve filter for injection of fluid in vivo, e.g., for a peritoneal dialysis treatment, when such treatment is needed and the patient's detachable filter 10 is unavailable, is microbicidally depleted below the safe level, or has become contaminated in some other way.

Figure 5:
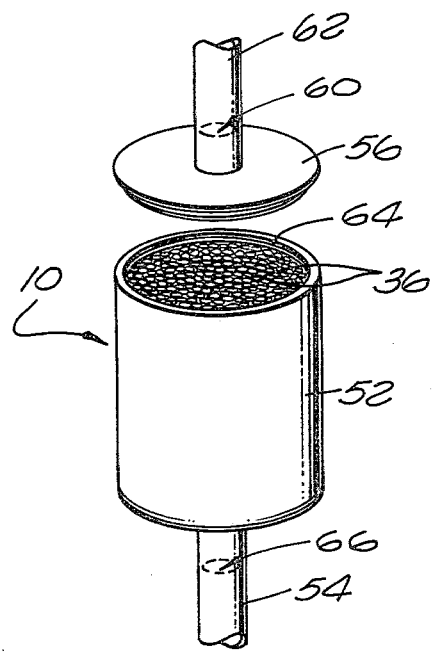
FIG. 5 shows a further alternative embodiment of the present invention in which the microbicidal filter is formed integrally with the external end of a body-piercing apparatus, e.g., a cannula, and has a removable top so that the filter elements may be removed and replaced after the microbicidal filtering capability of the elements packed within the filter has decreased to a selected level.

An additional embodiment of the invention is shown in FIG. 5. In the embodiment of FIG. 5, the filter 10 is formed in the shape of a cup-like expansion 52 having an integral tubular outlet coupling 54 which is formed integrally with the external end of the cannula 14. Thus the embodiment of FIG. 5 is intended to be worn at all times by the patient when the cannula 14 is inserted in the patient. The filter 10 shown in FIG. 5 has a detachable top 56 containing threads 58 and a tubular inlet coupling 62. The tubular inlet coupling 62 is shown to contain an inlet porous plate 60. Threads 64 contained in the open end of the cup-like expansion 52 enable the detachable top 56 to be screwed into place sealing the filter elements 36 within the cup-like expansion 52. A porous outlet plate 66 is shown to be contained within the tubular outlet coupling 54. The filter elements 36 are placed in the tubular expansion 52 in the sterile and antiseptic environment of, e.g., the doctor's office or hospital, and the detachable top 56 threaded into place and sealed by any suitable means against the invasion of microbes through the threaded connection of the detachable top 56 into the tubular expansion 52. Since the filter 10 of FIG. 5 is intended to be worn during the entire time that the cannula is in place in the patient's body, the detachable top enables removing and replacing the filter elements 36 as necessary to preserve the microbicidal effectiveness of filter 10.

In each of the embodiments discussed above, there is some chance of excessive silver migration in the filtered fluid from the filter elements 36. In order to insure that the silver content in the fluid to be injected in vivo does not exceed 800 ppb, a suitable silver ion exchange resin (not shown) may be positioned downstream of the filter elements 36 in the filter 10 or both the filter elements 36 in the filter 10 and in the auxiliary filter 72, when one is used.

SUMMARY OF THE ADVANTAGES AND SCOPE OF THE INVENTION

It will be appreciated that in using the method and apparatus for filtering microorganisms from a fluid to be injected in vivo according to the present invention, certain significant advantages are provided.

In particular, the significant problem of infection due to microorganisms contained within the solution to be injected in vivo is eliminated. This is of significant importance for self-administered injection of fluids into the patient's body in other than the sterile and antiseptic environment of, e.g., the hospital or doctor's office. This is particularly important for procedures such as peritoneal dialysis which free the patient from the bounds of a hospital or doctor's office to perform the necessary dialysis, but which in the past have suffered from the real and present danger of infection, e.g., peritonitis, resulting from microorganisms in the dialysis fluid or injection apparatus being injected into the body of the patient.

The filter apparatus and method according to the present invention in the embodiments intended to be permanently attached to the patient-penetrating apparatus, e.g., a cannula, provide a simple, light-weight microorganism filter which is effective to remove essentially 100% of the living microorganisms from the fluid, e.g, peritoneal dialysis solution, prior to entry of the solution into the patients's body. In the embodiments shown in which the filter is intended to be detachable between injections of fluid into the patient's body, e.g., for peritoneal dialysis, the auxiliary filter extension of the cannula is extremely useful to prevent infection due to injection of microorganisms. The auxiliary filter can be sterilly and antiseptically attached as an extension of the cannula in the doctor's office or hospital. It provides the added safeguard of eliminating any microorganisms which may infect the portion of the detachable filter, according to the present invention, downstream of the microbicidal filter elements, resulting from microorganism contamination of that portion of the filter (and also of the inlet inlet of the auxiliary filter) between patient treatments or in the course of connecting the detachable filter to the cannula.

The foregoing description of the invention has been directed to a particular preferred embodiment in accordance with the requirements of the patent statutes and for purposes of explanation and illustration. It will be apparent, however, to those of ordinary skill in this art that many modifications and changes in both the apparatus and method of the present invention may be made without departing from the scope and spirit of the invention. For example, the particular size and shape of the filter according to the present invention may be modified so long as the solution to be injected into the body of the patient is passed through a bed of filter elements composed of or coated with a microbicidal material, with the length of the passage through the bed of filter elements and the amount of spacing between the filter elements being sufficient to insure that essentially 100% of the living microorganisms in the solution will be exterminated during passage through the filter. The spherical shape of the filter elements is convenient for the purposes of manufacture of the filter elements and also for the purposes of minimizing the available flow passage between a plurality of adjacent filter elements. However, the filter elements of other shapes may also prove to be suitable. The filter may also be a multiple-pass filter, as shown in FIG. 3 having more than the two passes which are shown in FIG. 3. The porous plates may be placed as desired within the filter or in the tubular inlet and outlet couplings of the filter and may be of any suitable material having a sufficiently small porosity to retain the filter elements within the confines of the filter, and specifically to prevent the injection of any filter elements into the patient's body, while not being too restrictive of the flow of solution to be injected into the patient's body. In the case of the filters designed to be detached between treatments by the patient, the inlet porous plate, which prevents the filter elements from leaving the filter during backflushing of the solution from the patient's body, e.g., during draining of the peritoneal dialysis solution, may be eliminated.

It will further be apparent that the invention may also be used with other suitable modifications within the state of the art. Some of these include the various available methods and apparatus for connecting the tubing from the source of the solution to be injected into the body and for connecting the outlet of the filter to the cannula, in those embodiments where the filter is detachable. These can include the use of self-sealing membranes in the inlet and of the filter and outlet end of the filter, in which event the self-sealing membrane would act as the tubular inlet coupling and tubular outlet coupling. In this event the tube from the source of the solution to be injected would have a suitable means for penetrating the respective self-sealing membrane, and the external end of the cannula, in the embodiment in which the filter is detachable from the cannula, would also have a suitable means for penetrating the respective self-sealing membrane. Such a self-sealing membrane could also be placed in the tubular inlet coupling and, in the embodiment where the filter is detachable from the cannula, in the tubular outlet coupling. Numerous other methods and apparatus for connecting the filter between the source of the fluid to be injected and the external end of the cannula or other body-penetrating apparatus, which can either be used to be attached to the tubular inlet and tubular outlet couplings, or directly to the casing of the filter will be well within the skill of those in the art.

These and other modifications of the invention will be apparent to those skilled in the art. It is Applicant's intention in the following claims to cover all such equivalent modifications and variations as fall within the true spirit and scope of the invention.

What is claimed is:

1. A microorganism filter for use in removing living microorganisms from fluids to be introduced in vivo comprising:
   a housing defining a tubular fluid flow passage having a tubular wall, an inlet end and an outlet end, the outlet end in fluid communication with a passage in vivo, said housing further including a fist end enclosure plate, and second end enclosure plate;
   a first coupling at the inlet end forming a connecting means for connecting a source of fluid to the inlet end of the housing;
   a second coupling at the outlet end forming a coupling means for connecting the outlet to an in vivo passage;
   said first end enclosure plate having an opening placing the tubular passage in fluid communication with the first coupling;
   said second end enclosure plate having an opening placing the tubular passage in fluid communication with the second coupling;
   a plurality of filter elements having, on the surface thereof exposed to the fluid passing through the filter, a material having microbicidal properties, contained within the flow passage.
   a porous outlet retainer plate, disposed in the flow path of the fluid, downstream of the filter elements, and having openings sufficiently small to prevent passage of any of the plurality of filter elements through the outlet end of the housing, said outlet retainer plate being displaced from the second end enclosure plate to form an outlet plenum therebetween;
   a porous inlet retainer plate disposed between the first end enclosure plate and the filter elements and having openings sufficiently small to prevent passage of the filter elements through the inlet retainer plate;
   a tubular auxiliary filter disposed between the end of the second coupling and the external end of the in vivo passage; and
   the tubular auxiliary filter containing a plurality of the filter elements.

2. The apparatus of claim 1 further comprising:
   the tubular auxiliary filter has substantially the same inner diameter as the external end of the in vivo passage.

* * * * *